United States Patent
Dragar et al.

(10) Patent No.: US 10,149,874 B2
(45) Date of Patent: Dec. 11, 2018

(54) METHODS FOR DEPYROGENATING A SEAWEED EXTRACT

(71) Applicant: MARINOVA PTY LTD, Cambridge, Tasmania (AU)

(72) Inventors: Charles Dragar, New Town (AU); Janet Helen Fitton, Cambridge (AU); Vicki-Anne Gardiner, Cambridge (AU); Damien Stringer, Cambridge (AU); Samuel Karpiniec, Cambridge (AU)

(73) Assignee: MARINOVA PTY LTD, Cambridge, Tasmania (AU)

( * ) Notice: Subject to any disclaimer, the term of this patent is extended or adjusted under 35 U.S.C. 154(b) by 454 days.

(21) Appl. No.: 14/763,434

(22) PCT Filed: Dec. 20, 2013

(86) PCT No.: PCT/AU2013/001504
§ 371 (c)(1),
(2) Date: Jul. 24, 2015

(87) PCT Pub. No.: WO2014/113836
PCT Pub. Date: Jul. 31, 2014

(65) Prior Publication Data
US 2015/0359828 A1    Dec. 17, 2015

Related U.S. Application Data

(60) Provisional application No. 61/756,570, filed on Jan. 25, 2013.

(51) Int. Cl.
*A61K 31/737* (2006.01)
*A61K 36/03* (2006.01)
*A61K 36/02* (2006.01)

(52) U.S. Cl.
CPC .......... *A61K 36/03* (2013.01); *A61K 31/737* (2013.01); *A61K 36/02* (2013.01); *A61K 2236/00* (2013.01)

(58) Field of Classification Search
None
See application file for complete search history.

(56) References Cited

U.S. PATENT DOCUMENTS

| | | | | |
|---|---|---|---|---|
| 4,315,919 A | * | 2/1982 | Shanbrom | A61L 2/0088 424/520 |
| 6,451,772 B1 | * | 9/2002 | Bousman | A61K 9/0019 424/282.1 |
| 2004/0087545 A1 | | 5/2004 | Fritton et al. | |
| 2010/0144667 A1 | * | 6/2010 | Shaklee | A61K 31/737 514/54 |
| 2011/0168635 A1 | * | 7/2011 | Bender | A61L 24/001 210/663 |
| 2013/0065851 A1 | * | 3/2013 | Fitton | A61K 31/737 514/56 |

FOREIGN PATENT DOCUMENTS

| WO | 2000029449 A1 | 5/2000 |
|---|---|---|
| WO | 2008103234 A1 | 8/2008 |
| WO | 2009027057 A1 | 3/2009 |
| WO | WO2011100805 A1 | 8/2011 |
| WO | 2012138885 A1 | 10/2012 |

OTHER PUBLICATIONS

Williams, Kevin. Drugs and the Pharmaceutical Sciences, vol. 167 by Informa Healthcare, 2007. Chapter 15 entitled Depyrogenation, Validation, Pyroburden and Endotoxin Removal, pp. 301-327. (Year: 2007).*
International Search Report dated Jan. 29, 2014 for corresponding International Patent Application No. PCT/AU2013/001504, filed Dec. 20, 2013.
International Written Opinion dated Jan. 29, 2014 for corresponding International Application No. PCT/AU2013/001504, filed Dec. 20, 2013.

* cited by examiner

*Primary Examiner* — Ralph J Gitomer
(74) *Attorney, Agent, or Firm* — David D. Brush; Westman, Champlin & Koehler, P.A.

(57) ABSTRACT

A method is provided for treating a seaweed extract having a target molecule and a pyrogenic agent. The method includes inactivating the pyrogenic agent and/or removing the pyrogenic agent. The method results in a reduction in pyrogenicity of the extract. The method is useful in the preparation of pharmaceutical compositions and biomaterials for which pyrogen removal is critical.

10 Claims, No Drawings

METHODS FOR DEPYROGENATING A SEAWEED EXTRACT

CROSS REFERENCE TO APPLICATIONS

This application claims the benefit of U.S. Provisional Patent Application 61/756,570 filed 25 Jan. 2013, the contents of the specification of which is incorporated herein by reference in its entirety.

The present application is a Section 371 National Stage Application of International Application No. PCT/AU2013/001504, filed Dec. 20, 2013, which is incorporated by reference in its entirety and published as WO 2014/113836 A1 on Jul. 31, 2014, in English.

FIELD OF THE INVENTION

The present invention relates to methods for the treatment of extracts from marine organisms such as seaweed. More particularly, the present invention relates to the production of substantially pyrogen-free extracts useful in the manufacture of parenteral pharmaceutical compositions for use in wound management and surgery.

BACKGROUND TO THE INVENTION

A significant amount of work has been devoted to demonstrating biological activities of various seaweed components, including polysaccharide components such as fucoidan and ulvan. Fucoidan is a sulfated polysaccharide found in the cell walls of many species of brown seaweed. In vitro studies show that fucoidan has antitumor, antiangiogenic (Maruyama H, Tamauchi H, Hashimoto M, Nakano T. Antitumor activity and immune response of Mekabu fucoidan extracted from Sporophyll of *Undaria pinnatifida*. In Vivo 2003; 17 (3):245-249; Haneji K, Matsuda T, Tomita M et al. Fucoidan extracted from *cladosiphon okamuranus* tokida induces apoptosis of human T-cell leukemia virus type 1-infected T-cell lines and primary adult T-cell leukemia cells. Nutr. Cancer 2005; 52 (2):189-201; Liu J M, Bignon J, Haroun-Bouhedja F et al. Inhibitory effect of fucoidan on the adhesion of adenocarcinoma cells to fibronectin. Anticancer Res. 2005; 25 (3B):2129-2133; Koyanagi S, Tanigawa N, Nakagawa H, Soeda S, Shimeno H. Oversulfation of fucoidan enhances its anti-angiogenic and antitumor activities. Biochem. Pharmacol. 2003; 65 (2):173-179; Alekseyenko T V, Zhanayeva S Y, Venediktova A A, et al. Antitumor and antimetastatic activity of fucoidan, a sulfated polysaccharide isolated from the Okhotsk Sea *Fucus evanescens* brown alga. Bull. Exp. Biol. Med. 2007 June; 143 (6):730-2; Nagamine T, Hayakawa K, Kusakabe T, et al. Inhibitory effect of fucoidan on Huh7 hepatoma cells through downregulation of CXCL12. Nutr. Cancer 2009; 61 (3):340-7), antiviral (Lee J B, Hayashi K, Hashimoto M, Nakano T, Hayashi T. Novel antiviral fucoidan from sporophyll of *Undaria pinnatifida* (Mekabu). Chem. Pharm. Bull. (Tokyo) 2004 September; 52 (9):1091-4; Hayashi K, Nakano T, Hashimoto M, Kanekiyo K, Hayashi T. Defensive effects of a fucoidan from brown alga *Undaria pinnatifida* against herpes simplex virus infection. Int. Immunopharmacol. 2008 January; 8 (1):109-16.), and immunomodulatory effects (Raghavendran H R, Srinivasan P, Rekha S. Immunomodulatory activity of fucoidan against aspirin-induced gastric mucosal damage in rats. Int. Immunopharmacol. 2011 February; 11 (2):157-63). These effects are brought about by stimulating natural killer cells and by down regulating AP-I involved in cellular proliferation. Fucoidan also exhibited neuroprotective (Do H, Pyo S, Sohn E H. Suppression of iNOS expression by fucoidan is mediated by regulation of p38 MAPK, JAK/STAT, AP-1 and IRF-1, and depends on up-regulation of scavenger receptor B1 expression in TNF-alpha- and IFN-gamma-stimulated C6 glioma cells. J. Nutr. Biochem. 2009 Jul. 1; Luo D, Zhang Q, Wang H, et al. Fucoidan protects against dopaminergic neuron death in vivo and in vitro. Eur. J. Pharmacol. 2009 Sep. 1; 617 (1-3):33-40, radioprotective (Byon Y Y, Kim M H, Yoo E S, et al. Radioprotective effects of fucoidan on bone marrow cells: improvement of the cell survival and immunoreactivity. J. Vet. Sci. 2008 December; 9 (4):359-65), and antiulcer (Choi J I, Raghavendran H R, Sung N Y, et al. Effect of fucoidan on aspirin-induced stomach ulceration in rats. Chem Biol Interact. 2010 Jan. 5; 183 (1):249-54) properties.

In other studies, fucoidan demonstrated anticoagulant (Colliec S, Fischer A M, Tapon-Bretaudiere J, et al. Anticoagulant properties of a fucoidan fraction. Thromb. Res. 1991 Oct. 15; 64 (2):143-54; Irhimeh M R, Fitton J H, Lowenthal R M. Pilot clinical study to evaluate the anticoagulant activity of fucoidan. Blood Coagul. Fibrinolysis. 2009 Aug. 18) and antithrombotic (Church F C, Meade J B, Treanor R E, Whinna H C. Antithrombin activity of fucoidan. The interaction of fucoidan with heparin cofactor II, antithrombin III, and thrombin. J. Biol. Chem. 1989 Feb. 25; 264 (6):3618-23) activities, and can have additive effects when taken with anticoagulants.

Fucoidan has also shown particular promise in the prevention of post-surgical adhesions. The study of Cashman et al (Cashman J D, Kennah E, Shuto A, Winternitz, Springate C M K, Fucoidan Film Safely Inhibits Surgical Adhesions in a Rat Model, J. Surg. Res. 2011 December 171 (2):495-503) trialled a number of compounds but identified fucoidan as the safest and most efficacious. Fucoidan loaded films reduced adhesion scores by approximately 90% compared with control films. A total of 50% to 100% of animals were adhesion free at fucoidan film loadings of 0.33% to 33% w/w compared with all control film animals having adhesions. No adverse effects were observed from 33% w/w fucoidan films equivalent to approximately 30 mg fucoidan/kg body weight.

Fucoidan is also proposed to be useful in wound management, and particularly the healing of burns. Reference is made to the work of Sezer et al (Sezer A D, Hatipoglu F, Cevher E, Oğurtan Z, Bas A L, and Akbuğa J, Chitosan film containing fucoidan as a wound dressing for dermal burn healing: Preparation and in vitro/in vivo evaluation, AAPS Pharm. Sci. Tech. 2007 June; 8 (2): E94-E101). These authors demonstrated in a rabbit burn model that the best regenerated dermal papillary formation, best reepithelization, and the fastest closure of wounds were found in a fucoidan-chitosan film treatment group.

Ulvan (which is analogous to fucoidan) is extracted from green seaweed, and has potential in clinical applications. For example, ulvan holds significant promise as a scaffold in the manufacture of biomaterials, as a drug delivery vehicle, and also as an immune modulator.

It will be evident from the foregoing that polysaccharides extracted from marine organisms have the potential for use in diverse and clinically important applications. A significant problem in exploiting the benefits of these molecules is the presence of pyrogenic agents in the extracts. Where the disease indication requires parenteral administration, direct application to a wound or a surgical site, or implantation within the body, the use of these polysaccharide extracts is contraindicated due to the associated dangers of pyrogen-induced fever, toxic shock and even death.

"Microbial pyrogen" as opposed to "gram negative bacterial endotoxin" has become a general descriptive term for many different substances. However, pyrogenic substances can be produced by some gram positive bacteria, mycobacteria, fungi and also viruses, but the pyrogens produced by gram negative bacteria, i.e., the endotoxins, are of significance to the pharmaceutical and medical implant industry.

The prior art discloses a range of methods for depyrogenation of solutions for use in medicine. Many methods rely on the destruction of the pyrogenic agent. However, such methods often result in damage or destruction of a desired molecule in solution. This is particularly the case where the desired molecule is naturally derived.

Other methods of depyrogenation are directed to the physical removal of the pyrogenic agent by means such as chromatography and filtration. While such methods are clearly more suitable for the treatment of solutions containing labile molecules, significant problems arise in the scale up of these methods to the processing of commercial quantities. Often, industrial scale separative methods are not economically feasible due to the cost of media, and the need to constantly replace or regenerate the medium. Seaweed extracts in particular are known to contain residues and precipitates that cause blockage or fouling of separative media.

A further problem with seaweed extracts is the presence of an undesirable brown discolouration that often occurs during processing. This colouration is thought to be caused by the use of alkaline conditions, and typically carries through to the final product. Where the extract is formulated as a human injectable composition, an uncoloured solution is highly preferred to facilitate visual inspection of the injectate prior to administration.

It is an aspect of the present invention to overcome or alleviate a problem of the prior art by providing improved methods for treating seaweed extracts to decrease pyrogenicity and/or colouration. It is a further aspect to provide an alternative to existing methods of treatment.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

In a first aspect the present invention provides a method of treating a seaweed extract comprising a target molecule and a pyrogenic agent, the method comprising the step(s) of: inactivating the pyrogenic agent and/or removing the pyrogenic agent, wherein the method results in a reduction in pyrogenicity of the extract. The method may comprise contacting the extract with an effective amount of one or more of the following: an oxidant (such as a peroxide), a surfactant (such as a non-ionic surfactant), a base (such as a hydroxide), an activated carbon, a zeolite.

The target molecule may be a polysaccharide, and preferably a polysaccharide such as fucoidan or ulvan.

Preferred combinations within the method include (i) oxidant and base, (ii) oxidant, base and surfactant, (iii) activated carbon and base.

In another aspect, the present invention provides a substantially depyrogenated marine organism extract. The treated extract may have a level of pyrogenic agent less than about 100 EU/mg, as determined by LAL, and/or is capable of passing the rabbit pyrogenicity test. The extract may be produced by a method as described herein.

Also provided is a pharmaceutical composition comprising a substantially depyrogenated marine organism extract as described herein in combination with a pharmaceutically acceptable excipient.

A further aspect of the present invention is a method for treating or preventing a condition comprising administration of a pharmaceutical composition or implantation of a biomaterial as described herein to a mammal in need thereof.

Another aspect provides the use of the pharmaceutical composition or a biomaterial as described herein in medicine. Also provided is the use of a substantially depyrogenated marine organism extract as described herein, or a pharmaceutical composition as described herein in the manufacture of a medicament for the treatment or prevention of a condition.

DETAILED DESCRIPTION OF THE INVENTION

After considering this description it will be apparent to one skilled in the art how the invention is implemented in various alternative embodiments and alternative applications. However, although various embodiments of the present invention will be described herein, it is understood that these embodiments are presented by way of example only, and not limitation. As such, this description of various alternative embodiments should not be construed to limit the scope or breadth of the present invention. Furthermore, statements of advantages or other aspects apply to specific exemplary embodiments, and not necessarily to all embodiments covered by the claims.

Throughout the description and the claims of this specification the word "comprise" and variations of the word, such as "comprising" and "comprises" is not intended to exclude other additives, components, integers or steps.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may.

In a first aspect, the present invention provides a method of treating a seaweed extract comprising a target molecule and a pyrogenic agent, the method comprising the step(s) of: inactivating the pyrogenic agent and/or removing the pyrogenic agent, wherein the method results in a reduction in pyrogenicity of the extract.

The applicant has found that extracts of seaweeds and sea animals may be effectively depyrogenated, rendering them safe for human use. Importantly and unexpectedly, the removal and inactivation has been shown to result in insubstantial adverse effects on active target molecules present in the extract. Furthermore, recoveries of the target molecules have been shown to be commercially acceptable.

In one embodiment, the target molecule is a polysaccharide, and preferably a sulphated polysaccharide. The polysaccharide in one embodiment is a fucoidan or an ulvan.

As will be appreciated from the foregoing Background section, this discovery is a significant advance in the art, allowing for the more full investigation of the in vivo medical applications of active molecules in sea organisms such as fucoidan and ulvan, and also potentially the routine use of these actives in pharmaceutical formulations, or in the fabrication of medical implants.

In one embodiment of the method the step of inactivating the pyrogenic agent comprises contacting the extract with an effective amount of one or more of the following: an oxidant, a surfactant, a base, an activated carbon, a zeolite.

Without wishing to be limited by theory, where the method comprises use of an oxidant it is proposed that the oxidant acts to inactivate the pyrogenic agent. However, it was noted that levels of oxidant which were effective in reducing pyrogenicity did not induce substantial deleterious changes to a polysaccharide molecule of the extract. In some embodiments, a fucoidan molecule or an ulvan molecule substantially retains biological activity. As used herein, the term "biological activity" refers to any ability of the target molecule to induce a structural and/or functional change to a biological molecule, or to induce a change in a biological system or pathway, or to act as a biomaterial, or to act as a drug delivery agent in a biological system.

Common oxidants include molecular oxygen, ozone, hydrogen peroxide ($H_2O_2$) and other inorganic peroxides, fluorine ($F_2$), chlorine ($Cl_2$), and other halogens, nitric acid ($HNO_3$) and nitrate compounds, sulfuric acid ($H_2SO_4$), peroxydisulfuric acid ($H_2S_2O_8$), peroxymonosulfuric acid ($H_2SO_5$), chlorite, chlorate, perchlorate, and other analogous halogen compounds, hypochlorite and other hypohalite compounds, including household bleach (NaClO), hexavalent chromium compounds such as chromic and dichromic acids and chromium trioxide, pyridinium chlorochromate (PCC), and chromate/dichromate compounds, permanganate compounds such as $KMnO_4$, sodium perborate, nitrous oxide ($N_2O$), silver oxide ($Ag_2O$), osmium tetroxide ($OsO_4$), Tollens' reagent, and 2,2'-dipyridyldisulfide (DPS)

In one embodiment, the oxidant is an oxygen based oxidant such as a peroxide, ozone, or molecular oxygen. In one embodiment the oxidant is hydrogen peroxide. In order to potentiate the oxidation reaction, a catalyst such as a ferric ion may be included in the oxidation reaction mixture. An advantage of using peroxides is that coloured pigment complexes often found in seaweeds are bleached, thereby providing a substantially clear solution.

The amount of peroxide may depend on the species and purity of the extract, however ranges of about 10% to about 100% (w/w; by mass of peroxide to mass of polysaccharide) have been found effective. Experimental work disclosed herein demonstrates that an acceptable level of pyrogen reduction can be achieved with about 30% hydroxide (w/w of fucoidan) in the presence of 1% ferric citrate as catalyst. Accordingly, in one embodiment of the method the amount of peroxide is greater than about 30% (w/w).

The applicant has also demonstrated the effectiveness of surfactant treatment of seaweed extracts. Without wishing to be limited by theory in any way, it is proposed that pyrogenic agents are solubilised by a surfactant, with the solubilised agents being more readily inactivated (for example by an oxidant) or removed (for example by filtration). The surfactant may be a biological surfactant, of the type often used in biochemistry to solubilise cellular components and other naturally occurring molecules. The surfactant may be one useful in tissue culture, such as 3-(N,N-dimethylmyristylammonio)propanesulfonate, 3-(decyldimethylammonio) propanesulfonate inner salt zwitterionic detergent, ASB-14, Brij® 58 average $M_n$~1124, L-α-lysophosphatidylcholine from *Glycine max* (soybean) ≥99%, lyophilized powder, Brij® 58 main component: eicosaethylene glycol hexadecyl ether, Brij® L23 solution 30% (w/v), Brij® L23 main component: tricosaethylene glycol dodecyl ether, C7BzO, CHAPS, CHAPSO. Cholic acid, deoxycholic acid, digitonin, glycocholic acid, hexadecyltrimethylammonium bromide ≥98%, hexaethylene glycol monododecyl ether, IGEPAL CA-630, lithium dodecyl sulfate, N-decanoyl-N-methylglucamine, N-dodecyl-N,N-dimethyl-3-ammonio-1-propanesulfonate, N-nonanoyl-N-methylglucamine, Nonidet P-40, octyl D-glucopyranoside, octyl α-D-glucopyranoside, octyl β-D-1-thioglucopyranoside, Pluronic F-68, Polyoxyethylene (20), Polysorbate 20, Polysorbate 80, Saponin, sodium cholate hydrate, sodium deoxycholate, sodium dodecyl sulfate, sodium glycocholate hydrate, sodium taurodeoxycholate hydrate, Tween 20, Tween 40, Tween 80, taurocholic acid sodium salt hydrate, Triton X-100, Triton X-114, ursodeoxycholic acid, n-dodecyl β-D-maltoside, n-dodecyl β-D-maltoside.

The surfactant may be one useful in the solublisation of membranes and proteins such as 2-cyclohexylethyl β-D-maltoside, 3-(4-tert-Butyl-1-pyridinio)-1-propanesulfonate, 3-(N,N-dimethylmyristylammonio)propanesulfonate, 3-(1-pyridinio)-1-propanesulfonate, 3-(benzyldimethylammonio) propanesulfonate, 3-(decyldimethylammonio)propanesulfonate, 3-[N,N-dimethyl(3-palmitoylaminopropyl) ammonio]-propanesulfonate, 5-cyclohexylpentyl β-D-maltoside, ASB-14, ASB-C80, cyclohexylmethyl β-D-maltoside, decyl β-D-glucopyranoside, decyl β-D-maltopyranoside, decyl-β-D-1-thiomaltopyranoside, decyl-β-D-maltoside, dimethyldecylphosphine oxide, dimethylethylammoniumpropane sulfonate, dodecyltrimethylammonium chloride, EMPIGEN® BB detergent, hexadecylpyridinium chloride monohydrate, hexaethylene glycol monodecyl ether, isopropyl β-D-1-thiogalactopyranoside, isopropyl β-D-thiogalactopyranoside, Lutrol® OP 2000, MEGA-8, N,N-bis[3-(D-gluconamido)propyl]deoxycholamide, N-decanoyl-N-methylglucamine, N-dodecyl-N,N-dimethyl-3-ammonio-1-propanesulfonate, N-lauroylsarcosine, N-nonanoyl-N-methylglucamine, nonaethylene glycol monododecyl ether, octaethylene glycol monodecyl ether, pentaethylene glycol monododecyl ether, poly(maleic anhydride-alt-1-decene), 3-(dimethylamino)-1-propylamine derivative, polyoxyethylene (20) sorbitan monolaurate, sodium taurodeoxycholate hydrate ≥95%, sucrose monodecanoate, n-heptyl β-D-thioglucopyranoside.

The surfactant may be a non-ionic surfactant. In one embodiment the non-ionic surfactant is an alcohol C12-15 ethoxylated with n moles of ethylene oxide (n may be about 12), an alkyl alcohol polyethoxylate nonionic surfactant G12 A12, a dodecanol ethoxylate non-ionic detergent, a dodecyl alcohol, an ethoxylated straight chain alcohol, a lauryl polyethylene glycol ether, polyethylene glycol monododecyl ether, a lauric alcohol ethoxylate, an exemaplary form being Teric G12A12 (ICI Chemicals), or equivalent.

In one embodiment, the non-ionic surfactant is a polysorbate, a polyoxyethylene derivative of sorbitan monolaurate. In one embodiment, the surfactant is one of the Tween series (or equivalent), and in one embodiment is Tween 80 (Sigma Aldrich), or equivalent.

In one embodiment, the non-ionic surfactant is one having a hydrophilic polyethylene oxide chain (optionally having about 9.5 ethylene oxide units) and an aromatic hydrocarbon lipophilic or hydrophobic group. The hydrocarbon group may be a 4-(1,1,3,3-tetramethylbutyl)-phenyl group. The surfactant may be one of the Triton series (Supelco) or an equivalent such as the Pluronic series (BASF), and particularly Triton X-100.

The surfactant may be used in amounts of at least about 10%, 15%, 20%, 25%, 30%, 35%, 40%, 45%, 50%, 55%, 60%, 65%, 70%, 75%, 80%, 85% and 90% (w/w; by mass of surfactant to mass of polysaccharide). In some embodiments, the surfactant is used in an amount of at least about 50% w/w which may result in a 10-fold reduction in pyrogen load.

In particular, Teric® G12A12, Tween® 20 and Triton® X100 added in 75% w/w proportions resulted in useful levels of pyrogen reduction.

A further advantage of the use of surfactants is that polysaccharide yields of up to 100% may be provided in some embodiments.

The method may comprise contacting the extract with a base. Without wishing to be limited by theory in any way, it is proposed that the base acts to inactivate the pyrogenic agent. The utility of alkaline conditions (i.e. pH>7) has been shown in the depyrogenation of marine organism extracts. Suitable bases may include metal oxides, hydroxides, alkoxides and ammonia. For industrial scale treatment of extracts, easily accessible and cost effective bases such as potassium hydroxide, sodium hydroxide, and calcium hydroxide may be suitable. In one embodiment, the pH is adjusted to a figure of from about 10.5 to about 11.0.

In one embodiment, the base is sodium hydroxide preferably in a solution of about 0.5 molar. In that embodiment, a volume of 50 mL which may be used in amounts of at least about 50 mL of the solution is added per gram of polysaccharide. Where 50 mL was used, acceptable reductions in pyrogen load were noted. Higher levels of hydroxide (50 mL of 0.1 M sodium hydroxide) resulted in reductions of 50%.

The activated carbon and zeolite are added to the extract in an amount sufficient to adsorb at least a proportion of pyrogenic agent present. Amounts of at least about 5%, 10%, 15%, 20%, 25%, 30%, 35%, 40%, 45%, and 50% (w/w; mass of adsorbent to mass of polysaccharide) may be used. Amounts of at least about 10% w/w have been shown to result in a reduction in pyrogen load.

It is to be understood that the use of the oxidant, surfactant, base, activated carbon and zeolite can be alone, or in any combination of 5, or in any combination of any 4, or in any combination of any 3, or in any combination of any two.

A preferred combination is that of oxidant and base. Experiments including treatment with MOH (where M=Na or K) at amounts ranging from 10-200% (w/w MOH to polysaccharide) of the polysaccharide mass and $H_2O_2$ (10%-100% w/w peroxide to polysaccharide) at various temperatures for various times have shown to act synergistically to provide significant pyrogen reductions.

In one embodiment, the amount of base is sufficient to result in a pH from about 7.0 to about 12.5. A preferred combination is that of oxidant, base and surfactant. While a combination of hydrogen peroxide and Teric-G12A12 did not yield a lower pyrogen load than straight peroxide treatment, the addition of a base (such as sodium hydroxide or potassium hydroxide resulted in a synergistic effect to lower pyrogen levels.

A further preferred combination is that of activated carbon and base. Activated carbon has been trialled in both acidic and alkaline conditions, with a significant reduction in pyrogen load observed for alkaline conditions, but not for acidic.

Where the method comprises the step of removing the pyrogenic agent, the method comprises the step(s) of binding the extract to one or more of the following: an activated carbon, a zeolite, a ligand capable of substantially specifically binding to the pyrogenic agent, and substantially separating the bound pyrogenic agent from the target molecule. The skilled artisan is familiar with many methods by which the separation may be achieved. For example, a batch processing method may be utilized whereby a predetermined volume of extract is treated in a vessel and the bound pyrogenic agent separated away from the target molecule by settling or flocculating the complexes. Alternatively, the bound pyrogenic agent may be separated by a centrifugation technique, or by magnetic bead separation means.

In one embodiment, the ligand capable of substantially specifically biding to the pyrogenic agent is polymyxin B.

Standard preparative chromatographic methods are known to the skilled artisan, as demonstrated in the text *Preparative Chromatography* (Edited by H. Schmidt-Traub et al, Second Edition, 2012, Wiley-VCH Weinheim), the contents of which is herein incorporated by reference.

The methods of the present invention may include a hydrolysis step, and optionally a fractionation step to provide polysaccharide fragments of varying molecular weights. Investigations have been carried out on the bioactivities of various molecular weight fractions of the same polysaccharide source, with significant differences being found. It has been found that a higher molecular weight fraction of fucoidan was more effective than an unfractionated crude fucoidan in inhibiting liver fibrosis (Nakazato et al; *Attenuation of N-nitrosodiethylamine-induced liver fibrosis by high-molecular-weight fucoidan derived from Cladosiphon okamuranus.* J. Gastroenterol. Hepatol. 2010;25: 1692-1701). Another study compared three different fractions of fucoidan in mice (Shimizu et al; *Proportion of murine cytotoxic T-cell is increased by high-molecular weight fucoidan extracted from Okinawa Mozuku (Cladosiphon okamuranus)* J. Health Sci. 2005;51:394-397). This study demonstrated differential immune effects, with greater increases in CD8 expression in spleens of animals fed high molecular weight fucoidan fractions as compared with those fed lower molecular weight fucoidan.

The hydrolysis may be partial or complete, and may be achieved by acidic conditions, enzymatic treatment or any other means known to the skilled person.

The fractionation may be achieved by well known methods such as chromatographic means (for example by the use of size exclusion resins such as Sepharose) or ultrafiltration for example.

Alternatively, the methods may be applied to already hydrolysed and/or fractionated polysaccharide preparations.

Advantageously, some embodiments of the method provide for a commercially desirable yield of polysaccharide, while still providing an effectively depyrogenated product. The yield may be greater than about 40%, 45%, 50%, 55%, 60%, 65%, 70%, 75%, 80%, 85%, 90%, 395 95% or 100%. In one embodiment, the yield is greater than about 30%. In another embodiment the yield is greater than about 60%. While the aforementioned yield is expressed on the basis of weight of polysaccharide recovered, it is understood that biological activity or other suitable parameters may be used in place.

The applicant has demonstrated the further advantage of the scalability of the present methods by demonstrating commercially useful recoveries of a target fucoidan using kilogram quantities of dried fucoidan product while still reducing the pyrogen load by 99%. Reference is made to Example 20 herein. In some embodiments, the method is capable of utilizing at least about 0.1 kg, 0.5 kg, 1 kg, 2 kg, 3 kg, 4 kg, 5 kg, 6 kg, 7 kg, 8 kg, 9 kg, 10 kg, 20 kg, 30 kg, 40 kg, 50 kg, 60 kg, 70 kg, 80 kg, 90 kg or 100 kg of dried polysaccharide as starting material.

The inactivation or removal of the pyrogenic agent may be measured by any method known to the skilled artisan. One suitable test is the Limulus Amebocyte Lysate (LAL) assay. A number of kits are available, such as the "Chromo-LAL" kit sold by Associates of Cape Cod Incorporated (MA). In this test, co-lyophilized LAL and substrate reagent are mixed with the test sample in a microplate and incubated in a reader at 37±1 ° C. Absorbance measurements are collected with time after addition of Chromo-LAL and analyzed by suitable software. The time (onset time) taken for a sample to reach a specified absorbance (onset OD) is calculated; and a standard curve, showing the linear correlation between the log onset time and the log concentration of standard endotoxin, is generated. The maximum range of endotoxin concentrations for the standard curve is 0.005 EU/mL-50 EU/mL. The sensitivity (A) of the assay is defined as the lowest concentration used in the standard curve. The maximum sensitivity of this test is 0.005 EU/mL.

The endotoxin concentration for the corresponding onset time of the unknown sample is read from the standard curve which is a log-log plot of the onset times vs. the standard concentrations, or an arithmetic plot of the logs of onset times vs. the logs of the standard concentrations. The log-log line equation generated for an exemplary standard curve is $Y=-0.2X+3.14$, where $Y=\log$ onset time and $X=\log$ endotoxin concentration. The concentration of endotoxin in an unknown sample with a mean onset time of 1630 seconds would be calculated by converting the onset time to its log value, 3.212, solving the equation for X, and taking the antilog of X to obtain concentration:

$$X=(Y-3.14)/-0.2$$

$$X=(3.212-3.14)/-0.2$$

$$X=-0.36$$

Antilog(−0.36)=0.44 EU/mL (or EU/mg)

Typically, endotoxin levels in a seaweed extract as measured by an LAL are between 5,000 and 10,000 EU/mg. The depyrogenation methods of the present invention can reduce endotoxin to levels of less than about 9000, 8000, 7000, 6000, 5000, 4000, 3000, 2000, 1000, 900, 800, 700, 600, 500, 400, 300, 200, 100, 90, 80, 70, 60, 50, 40, 30, 20, 10, 9, 8, 7, 6, 5, 4, 3, 2, or 1 EU/mg.

Another test which is useful for demonstrating the inactivation or removal of the pyrogenic agent is the US Pharmacopeia Rabbit Pyrogen Test (USP<151>). The Rabbit Pyrogen Test is an in vivo test to detect pyrogens qualitatively. Rabbits have a similar pyrogen tolerance to humans, so by observing a change in body temperature in rabbits it is possible to make a determination of the presence of pyrogens. This method can detect non-bacterial endotoxin pyrogens as well as bacterial endotoxins.

If no rabbit shows an individual rise in temperature of 0.5° C. or more above its respective control temperature when dosed with an appropriate amount of product, the product meets the requirements for the absence of pyrogens. If any rabbit shows an individual temperature rise of 0.5° C. or more, the test is continued using five other rabbits. If not more than three of the eight rabbits show individual rises in temperature of 0.5° C. or more and if the sum of the eight individual maximum temperature rises does not exceed 3.3° C., the material under examination meets the requirements for the absence of pyrogens.

In one embodiment of the method, injection of the treated extract results in no rabbit exhibiting an individual rise in temperature of 0.5° C. or more above its respective control temperature. Where testing is continued using 5 further rabbits, in one embodiment injection of the treated extract results in not more than three of the eight rabbits showing individual rises in temperature of 0.5° C. or more and the sum of the eight individual maximum temperature rises does not exceed 3.3° C.

Both the LAL and USP Rabbit Pyrogen Test are recognised by the United States Food and Drug administration as acceptable in the validation of safety of parenteral formulations.

In some embodiments of the method, at least about 1%, 5%, 10%, 15%, 20%, 25%, 30%, 35%, 40%, 45%, 50%, 55%, 60%, 65%, 70%, 75%, 80%, 85%, 90%, 95%, 99%, 99.9%, 99.99%, or 99.999% of pyrogenic agent is removed and/or inactivated. In one embodiment the pyrogenic agent is removed and/or inactivated to a level acceptable to a government regulatory agency such as the United States Food Drug administration, or the European Medicines Agency, or the Australian Therapeutic Goods Administration, or Health Canada; as the requirements of those agencies are specified at the filing date of this application. Preferably, the method provides at least about 50%, 90% or 99% removal and/or inactivation. In one embodiment, a fucoidan composition produced by the method is capable of producing a composition capable of passing the USP rabbit pyrogen test and/or the LAL test. In one embodiment the method is capable of producing a solution having a pyrogen level of less than about 100 EU/mL as measured LAL.

The marine organism extract may be obtained from a brown seaweed of the Class Phaeophyceae, Order Laminariales (e.g. Akkesiphycaceae, Alariaceae, Chordaceae, Costariaceae, Laminariaceae, Lessoniaceae and Pseudochordaceae) or Order Fucales (e.g. Bifurcariopsdaceae, Durvillaeaceae, Fucaceae, Himanthallaceae, Hormosiraceae, Notheiaceae, Sargassaceae and Seirococcaceae). Examples of Order Laminariales seaweed includes species of the Genus *Undaria* such as but not limited to *Undaria pinnatifida*, or related species such as *Alaria esculenta, Saccorhiza polysaccharides, Undaria undarioides, Undaria peterseniana* and *Laminaria* sp such as *Laminaria digitata, Laminaria hyperborean, Laminaria ochroleuca, Laminaria saccharina, Laminaria agardhii, Laminaria angustata, Laminaria bongardina, Laminaria cuneifolia, Laminaria dentigera, Laminaria ephemera, Laminaria farlowii, Laminaria groenlandica, Laminaria japonica, Laminaria longicruris, Laminaria nigripes, Laminaria ontermedia, Laminaria pallida, Laminaria platymeris, Laminaria saccharina, Laminaria setchellii, Laminaria sinclairli, Laminaria solidungula* and *Laminaria stenophylla*. Examples of the Order Fucales seaweed include species of the Genus *Fucus* such as but not limited to *Fucus vesiculosus, Fucus ceranoides, Fucus chalonii, Fucus cottonii, Fucus distichus, Fucus evanescens, Fucus gardneri, Fucus nereideus, Fucus serratus, Fucus spermophorus, Fucus spiralis, Fucus tendo* and *Fucus virsoides*.

Other orders of brown seaweed include Ascoseirales, Cutleriales, Desmarestiales, Dictyotales, Discosporangiales, Extocarpales, Ishigeales, Nemodermatales, Onslowiales, Ralfsiales, Scytosiphonales, Scytothaminales, Sphacelariales, Sporochnales, Syringodermatales, Tilopteridales and Incertaesedis.

Particular brown seaweeds include species of *Ascoseira, Cutleria, Microzonia, Zanardinia, Arthrocladia, Desmarestia, Himantothallus, Phaeurism, Dictyopteris, Dictyota,*

*Dilophus, Distromium, Glossophora, Homoeostrichus, Lobophora, Lobospira, Newhousia, Pachydictyon, Padina, Spatoglossum, Stypopodium, Taonia, Zonaria, Scoresbyella, Choristocarpus, Discosporangium, Acinetospora, Feldmannia, Geminocarpus, Hincksia, Pogotrichum, Pylaiella, Adenocystis, Caepidium, Utriculidium, Acrothrix, Ascoseirophila, Asperococcus, Austrofilum, Chordaria, Cladosiphon, Corycus, Delamarea, Dictyosiphon, Elachista, Eudesme, Giraudia, Gononema, Halothrix, Haplogloia, Hecatonema, Heterosaundersella, Hummia, Isthmoplea, Laminariocolax, Laminar ionema, Leathesia, Leptonematella, Litosiphon, Microspongium, Mikrosyphar, Myelophycus, Myriogloea, Myrionema, Myriotrichia, Papenfussiella, Petrospongium, Pleurocladia, Polytretus, Proselachista, Protectocarpus, Punctaria, Sauvageaugloia, Soranthera, Sorocarpus, Spermaiochnus, Sphaerotrichia, Stictyosiphon, Streblonema, Striaria, Stschapovia, Tinocladia, Chordariopsis, Asterocladon, Ectocarpus, Kuckuckia, Mesospora, Asterotrichia, Bachelotia, Bifurcariopsis, Durvillaea, Ascophyllum, Fucus, Hesperophycus, Pelvetia, Pelvetiopsis, Silvetia, Xiphophora, Himanthalia, Hormosira, Notheia, Anthophycus, Axillariella, Bifurcaria, Bifurcariopsis, Carpoglossum, Caulocystis, Coccophora, Cystophora, Cystoseira, Halidrys, Hizikia, Hormophysa, Myagropsis, Myogropsis, Myriodesma, Sargassum, Turbinaria, Cystophaera, Marginariella, Phyllospora, Seirococcus, Ishige, Akkesiphycus, Alaria, Aureophycus, Druehlia, Eualaria, Hirome, Lessoniopsis, Pleurophycus, Pterygophora, Undaria, Undariella, Undariopsis, Chorda, Agarum, Costaria, Dictyoneurum, Thalassiophyllum, Arthrothamnus, Costularia, Cymathere, Feditia, Gigantea, Laminaria, Macrocystis, Nereocystis, Pelagophycus, Pelagophycus×Macrocystis, PhycoCastanum, Phyllariella, Polyschidea, Postelsia, Pseudolessonia, Saccharina, Streptophyllopsis, Ecklonia, Eckloniopsis, Egregia, Eisenia, Lessonia, Pseudochorda, Nemoderma, Onslowia, Verosphacella, Neoralfsia, Basispora, Hapalospongidion, Jonssonia, Lithoderma, Myrionemopsis, Petroderma, Porterinema, Pseudolithoderma, Ralfsia, Chnoospora, Colpomenia, Hydroclathrus, Petalonia, Rosenvingea, Scytosiphon, Bodanella, Coelocladia, Heribaudiella, Phaeostroma, Asteronema, Scytothamnus, Stereocladon, Splachnidium, Cladostephus, Sphacelaria, Sphacella, Alethocladus, Halopteris, Stypocaulon, Austronereia, Bellotia, Carpomitra, Encyothalia, Nereia, Perisporochnus, Perithalia, Sporochnema, Sporochnus, Tomaculopsis, Syringoderma, Halosiphon, Masonophycus, Phyllariopsis, Saccorhiza, Stschapovia, Haplospora, Phaeosiphoniella, Tilopteris, Neolepioneuma, Analipus* and *Phaestrophion*.

Particular brown seaweeds include species of *Adenocystis, Alaria, Ascophyllum, Chorda, Cladosiphon, Desmarestis, Dictyota, Durvillaea, Ecklonia, Ectocarpus, Egregia, Fucus, Halidrys, Himanthalia, Hormosiria, Lethesia, Lessonia, Macrocystis, Nereocystis, Padina, Pelagophycus, Pelvatia, Pilaiella, Postelsia, Saccrhiza, Sargassum, Sphacelaria* and *Turbinaria*.

Other suitable marine organisms include green seaweed and echinoderms such as sea urchins and sea cucumbers. Examples of green seaweed include *Ulva* sp, *Enteromorpha* sp, *Codium* sp, *Caulerpa* sp and *Halimala* sp.

In an embodiment, the extract is sourced from *Undaria pinnatifida, Fucus vesiculosus* or *Ulva* sp.

Fucoidan may also be derived from *Chorda filum, Cladosiphon okamuranus, Undaria pinnatifida, Leathesia difformis, Ascophyllum nodosum, Ecklonia kurome, Pelvetiafastigiata, Saundersella simplex,* or *Chordariaflagelliformis*.

Hence, the extract may be sourced from any brown or green seaweed or any echinoderm.

Where the marine organism is a plant, the extract may be sourced from the whole plant or any part of the plant, such as the leaves, stem, spores, or a combination thereof. The starting material for the preparation of the extract may be fresh, frozen or dried material.

The extract may be prepared using procedures such as maceration, exudation, decoction, extraction under reflux, extraction with aid of ultrasonics, extraction aided by partitioning between solvent phases and supercritical extraction with or without co-solvents. Acid or base treatment of seaweed may also be used to form an extract useful as a stating material for the present methods.

In one embodiment, the method is for the isolation of a carbohydrate and particularly for the isolation of a polysaccharide. The polysaccharide may be an alginate, or a sulphated polysaccharide.

In one embodiment the sulphated polysaccharide is a fucoidan, or a fucoidan derivative. In the context of the present invention, the term "fucoidan," is intended to mean a sulfated alpha-L-fucan, of the type found in many sea plants and animals.

In one embodiment, the sulphated polysaccharide is an ulvan, or an ulvan derivative. In the context of the present invention, the term "ulvan" is intended to mean a sulphated cell wall component from green algae consisting of varying degrees of sulphated rhamnose, xylose, glucuronic acid and iduronic acid residues.

In addition, the terms "fucoidan" and "ulvan" further includes biologically active fragments, derivatives, or analogues thereof. Also included are fragments of fucoidan or ulvan generated by degradation (e.g., hydrolysis) of larger molecules. Degradation can be achieved by treatment with acid, base, heat, or enzymes to yield degraded fucoidan or ulvan, which may or may not be isolated separately. Fucoidan and ulvan may also be chemically altered and may have modifications, including but not limited to, sulfation, polysulfation, acetylation, esterification, and methylation.

In one embodiment, the method is devoid of a step requiring the use of asbestos, lipopolysaccharide-detoxifying enzyme, guanidine hydrochloride, ammonium sulfate, a chromatographic resin, Acticlean endotox, immobilised histamine, or Triton silica, or any other depyrogenating filter commercially available at the filing date of this application.

In one aspect, the present invention provides a substantially depyrogenated marine organism extract. Preferably, the extract has a level of pyrogenic agent less than about 100 EU/mL, as determined by LAL, and/or is capable of passing the rabbit pyrogenicity test.

In another aspect, the present invention provides an extract produced by a method as described herein.

In one embodiment, the extract is produced by, at least in part, a method disclosed herein. It will be understood that the present methods may be augmented with other steps for the reduction and/or removal of pyrogenic agents.

Treated extracts may be analyzed for purity and various properties of the polysaccharide contained therein, such as molecular weight, carbohydrate content, including fucose, galactose, rhamnose, xylose, uronic acids, heavy metal contamination, sulfation, acetylation, counter-ions and water. A number of analytical techniques can be used to characterize polysaccharide samples, including but not limited to, high performance liquid chromatography (HPLC), elemental composition analysis, laser light scattering (LLS), inductively coupled plasma mass spectrometry (ICP-MS), Ultraviolet-visible spectroscopy (UV-Vis) and GC-MS. In some embodiments, the fucoidan in the treated extract is substantially similar with respect to the one or more of the aforementioned properties, when compared with the untreated fucoidan.

In another aspect, the present invention provides a pharmaceutical composition comprising a polysaccharide produced according to the methods described herein in combination with a pharmaceutically acceptable excipient. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

A composition of the invention may also comprise an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

The composition may comprise an antioxidant to inhibit oxidation, thereby preventing the deterioration of the fucoidan or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, polyphenols, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (BASF); sorbitan esters; lipids, such as phospholipids such as lecithin and other phosphatidylcholines, phosphatidylethanolamines, fatty acids and fatty esters; steroids, such as cholesterol; chelating agents, such as EDTA; and zinc and other such suitable cations.

Acids or bases may be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumarate, and combinations thereof.

In another embodiment, the present invention provides a biomaterial comprising a polysaccharide produced according to a method as described herein. Ulvan may be used as a biological cement (e.g. a bone cement) or to form a three-dimensional scaffold to facilitate the growth of new tissue. Moreover, ulvan may be used as a biodegradable hydrogel, and is potentially useful as a drug delivery vehicle. In that context the ulvan may be functionalized, for example by grafting radical polymerizable groups to attain biodegradable hydrogels.

The depyrogenated fucoidans of the present invention will have utility in one or more clinical applications or in sterile ex vivo applications, in particular as a modulator of coagulation, a fibrinolytic, as an anti-cancer agent, as an anti-viral agent (see in particular Applicant's published international patent application WO/2011/100805, the contents of which is herein incorporated by reference) or as a hematopoietic stem cell or other type stem cell mobilizing agent.

Other clinical indications for which the present depyrogenated fucoidan extracts may have utility include inflammation. The fucoidan may act via selectin blockade activity, scavenger receptor blockade and modulation of the accumulation of inflammatory cells. Acute and chronic inflammatory conditions including asthma, allergic dermatitis, cardiovascular disease, post ischemic inflammation, and inflammation subsequent to other infection or pathology.

Depyrogenated fucoidan extract may act as a stem cell mobilisation agent in the context of radiation and chemotherapy adjunct agent to protect stem cells of cancer patients. The extracts may be useful as a direct anti-cancer agent, or an adjunct anti-cancer agent. Therapeutic applications to gut disorders are further contemplated. In particular, gastric conditions caused by ethanol or other agents, or by infections such as Helicobacter pylori and clostridium difficile.

Antiviral applications are further contemplated, including the treatment of herpes virus infections (including HSV1, HSV2, and drug resistant strains thereof), cytomegalovirus (HCMV), influenza virus, HIV. Topical or oral delivery would be typical in these circumstances, although some Herpes infections may require direct application to the site via injection or other method.

Conditions involving immune modulation are also potentially amenable given the ability of fucoidan to enhance immune function including the numbers and activity of immune cells such as monocytes, NK cells and dendritic cells. Fucoidan is known to enhance the activity of these cells in order to produce an antipathogenic or anticancer effect.

A further contemplated use is in anti-adhesion therapy to prevent adhesions in surgical applications.

A further contemplated use is in the modulation of enzyme function including those related to coagulation, glucose metabolism, the modulation of matrix protein turnover and other enzymatic processes both ex vivo and in vivo. The present fucoidan extracts may also be employed to modulate the activity of growth factors such as TGFβ and their receptors.

The present depyrogenated extracts may be used in neural diseases (including those that depend on amyloid accumulation), in clotting disorders (including as an anti-thrombotic, thrombolytic, or anticoagulant, or procoagulant) as well as haemophilia, topical cosmetic creams, dental applications, ocular applications, and as a carrier for a radioactive marker for P selectin imaging. Furthermore, the present depyrogenated fucoidan extracts may be used as a release agent or carrier for antibiotics or other active agents.

The depyrogenated extracts may be delivered to the body by any suitable method, and to any part of the body as deemed necessary or appropriate by a clinician.

Accordingly, the present invention provides methods of treating such conditions in humans and other mammals using the compositions as described herein.

The present invention will now be more fully described by reference to the following non-limiting examples.

EXAMPLE 1

Depyrogenation of Fucoidan Purified from *Undaria pinnatifida*

The starting material was a freeze dried product previously purified for fucoidan, to about 87%, comprising neutral carbohydrates (approximately 50%-27.5% fucose, 22.5% galactose), sulfate (26%), acetyl moieties (3%) and counterions (8%).

All water used in this method was filtered through a depyrogenating filter before use. All equipment was sanitised and rinsed with depyrogenated water before use.

2.86 kg of the freeze dried fucoidan product was dissolved in 50-fold (143 L) of 0.05 M NaOH.

The dissolution was carried out by firstly placing about 114.4 L of DI water (i.e. 80% of 143 L) in a reaction vessel. 5.94 kg of NaOH was added to the DI water, and the remainder of the 143 L of DI water was added. The solid fucoidan (2.86 kg) was then added while mixing. The solution was heated to 40° C. while mixing until all solids were completely dissolved. The solution was then held at 40° C. for 10 minutes.

3 kg of Speedplus filter aid (Dicalite, PA) was added to the solution, and filtration was carried out using a pressure filter. 180 L of filtrate was collected, and transferred to a fresh reaction vessel.

2.6 L of $H_2O_2$ (50% w/w) was added to the filtrate, and the solution held at 60° C. for 1 hour while mixing. The solution was then allowed to cool to 45° C., and pH adjusted to 10.0 to 10.5 with $H_2SO_4$ (36% w/w). A final pH of 10.44 was achieved.

The pH adjusted solution was ultrafiltered using a membrane of 77 ft$^2$, with nominal cut-off of 30 kDa (Synder Filtration, CA)

The UF equipment was assembled and sanitized by recirculating a solution of 150 mL NaOCl per 100 L of DI water at 45 to 50° C., pH 10 to 11, for 30 minutes. The equipment was rinsed with at least 200 L of depyrogenated DI water. The fucoidan solution was added to the retentate vessel, and ultrafiltration performed until the retentate was concentrated to about 20% of the original volume. The feed pressure was maintained at 2.0 bar, and the retentate pressure at 1.0 bar through the ultrafiltration step. The permeate flux started at 12.5 L/minute, and had dropped to 10.8 L/minute at conclusion of the ultrafiltration.

The concentrated fucoidan solution (40 L) was then diafiltered using depyrogenated DI water (160 L). Feed pressure was maintained at 2.0 bar, retentate pressure at 1.0 bar. The permeate flux decreased from 10.9 L/minute to 7.5 L/minute over 20 minutes.

The pH was then adjusted to 8 with $H_2SO_4$, and diafiltration continued with another 4 volumes (160 L) of depyrogenated DI water. Feed pressure was maintained at 2.0 bar, retentate pressure at 1.0 bar. Permeate flux decreased from 7.5 L/minute to 6.0 L/minute over the 27 minutes of diafiltration.

The solution was then concentrated down to a volume of 40 L.

The concentrate was passed through a new Cuno 1 DEPL depyrogenating filter, and subsequently freeze dried. A total of 1820 g of solid was recovered. The freeze dried product was milled through a Comil 032 screen.

A process yield of 63% was calculated. A reduction in pyrogen of 90% (as measured by LAL) was noted.

EXAMPLE 2

Depyropenation of Fucoidan Purified from *Undaria pinnatifida* by Contact with Zeolite, Followed by Ultrafiltration Fucoidan (15.00 g) was dissolved in 300 mL of distilled water and filtered through a glass fibre filter. The filtrate was made up to 300 g with distilled water. A 40 mL aliquot of the fucoidan solution was diluted to 100 mL with distilled water and 0.2 g of zeolite was added. The suspension was stirred for 14 hours before being filtered through a glass fibre filter. The filtrate was then ultrafiltered through an Amicon stirred cell and the retentate washed with 100 mL of distilled water, before being concentrated to a final volume of 40 mL and freeze dried.

A reduction in pyrogen of 1% (as measured by LAL) was noted.

A similar process but without the zeolite contact step produced a fucoidan yield of 92.5%, with no reduction in pyrogen.

EXAMPLE 3

Depyrogenation of Fucoidan Purified from *Undaria pinnatifida* by Contact with Low Level Alkali and Activated Carbon, Followed by Ultrafiltration Fucoidan (15.00 g) was dissolved in 300 mL of distilled water and filtered through a glass fibre filter. The filtrate was made up to 300 g with distilled water. A 40 mL aliquot of the fucoidan solution was diluted to 100 mL with 0.5% NaOH and 0.2 g of activated carbon was added. The suspension was stirred for 14 hours before being filtered through a glass fibre filter. The filtrate was then ultrafiltered through an Amicon stirred cell and the retentate washed with 100 mL of depyrogenated distilled water, before being concentrated to a final volume of 40 mL and freeze dried. A reduction in pyrogen of 66% (as measured by LAL) was noted.

EXAMPLE 4

Depyrogenation of Fucoidan Purified from *Undaria pinnatifida* by Contact with Surfactant, Followed by Ultrafiltration Fucoidan (10.00 g) was dissolved in 300 mL of depyrogenated water. The solution was filtered through a glass fibre filter to yield a clear brown solution (~280 mL).

A 75_g aliquot of the fucoidan solution was diluted to 150 mL with distilled water and 1.8 g of Teric® G12A12 was added. The suspension was stirred for 1 hour before being filtered through a glass fibre filter. The filtrate was then ultrafiltered through an Amicon stirred cell and the retentate washed with 100 mL of depyrogenated distilled water, before being concentrated to a final volume of 40 mL and freeze dried. A reduction in pyrogen of 93% (as measured by LAL) was noted.

A 75 g aliquot of the fucoidan solution was diluted to 150 mL with distilled water and 1.8 g of Tween® 20 was added. The suspension was stirred for 1 hour before being filtered through a glass fibre filter. The filtrate was then ultrafiltered through an Amicon stirred cell and the retentate washed with 100 mL of depyrogenated distilled water, before being concentrated to a final volume of 40 mL and freeze dried.

A 75 g aliquot of the fucoidan solution was diluted to 150 mL with distilled water and 1.8 g of Triton® X100 was added. The suspension was stirred for 1 hour before being filtered through a glass fibre filter. The filtrate was then ultrafiltered through an Amicon stirred cell and the retentate washed with 100 mL of depyrogenated distilled water, before being concentrated to a final volume of 40 mL and freeze dried.

EXAMPLE 5

Depyrogenation of Fucoidan Purified from *Undaria pinnatifida* by Contact with Low Level Peroxide, Followed by Ultrafiltration Fucoidan (6.00 g) was dissolved in 250 mL of distilled water. The pH was held at 7.00 using an autotitrator dispensing 0.5 M NaOH. The solution was heated with stirring to 90° C. on a hot plate, then 3.0 mL of 30% w/w $H_2O_2$ was added. After 1 hour the reaction had consumed 4.37 mL of alkali. The solution was left to stand at room temperature overnight before being filtered through a glass fibre filter. The filtrate was then filtered through an Amicon stirred cell and the retentate washed with 50 mL of depyrogenated distilled water, before being concentrated to 50 mL and freeze dried.

A reduction in pyrogen of 83% (as measured by LAL) was noted.

EXAMPLE 6

Depyrogenation of Fucoidan Purified from *Undaria pinnatifida* by Contact with Peroxide in the Presence of Ferric Catalyst, Followed by Ultrafiltration Fucoidan (10.00 g) was dissolved in 250 mL of distilled water. The pH was held at 7.00 using an autotitrator dispensing 0.5 M NaOH. The solution was heated with stirring to 60° C. on a hot plate, then 10.0 mL of 30% w/w $H_2O_2$ and 0.1 g of FeIII citrate were added. After 4 hours, 14.92 mL of alkali was consumed. The solution was left to stand at room temperature overnight before being filtered through a glass fibre filter. The filtrate was then filtered through an Amicon stirred cell and the retentate washed with 50 mL of depyrogenated distilled water, before being concentrated to 50 mL and freeze dried.

A reduction in pyrogen of 94% (as measured by LAL) was noted.

EXAMPLE 7

Depyrogenation of Fucoidan Purified from *Undaria pinnatifida* by Contact with High Level Peroxide in the Presence of Ferric Catalyst, with Second Peroxide Treatment, Followed by Ultrafiltration Fucoidan (10.00 g) was dissolved in 250 mL of distilled water. The pH was held at 7.00 using an autotitrator dispensing 0.5 M NaOH. The solution was heated with stirring to 60° C. on a hot plate, then 10.0 mL of 30% w/w $H_2O_2$ and 0.1 g FeIII citrate were added. After 2 hours, 12.10 mL of alkali was consumed. Another 5.0 mL of 30% w/w $H_2O_2$ was added. After 10 hours a total of 15.23 mL of alkali had been consumed. The solution was left to stand at room temperature overnight before being filtered through a glass fibre filter. The filtrate was then filtered through an Amicon stirred cell and the retentate washed with 50 mL of depyrogenated distilled water, before being concentrated to 50 mL and freeze dried.

A reduction in pyrogen of 99% (as measured by LAL) was noted.

EXAMPLE 8

Depyrogenation of Fucoidan Purified from *Undaria pinnatifida* by Contact with High Level Peroxide in the Presence of Ferric Catalyst and Surfactant, Followed by Ultrafiltration Fucoidan (10.00 g) was dissolved in 250 mL of distilled water. The pH was held at 7.00 using an autotitrator dispensing 0.5 M NaOH. The solution was heated with stirring to 70° C. on a hot plate, then 10.0 mL of 30% w/w $H_2O_2$ and 0.1 g FeIII citrate were added. After 1 hour, 12.22 mL of alkali had been consumed. The solution was cooled and left at room temperature overnight before being filtered through a glass fibre filter. A 125 mL aliquot of the filtrate was treated with 2.0 g of Teric® G12A12 for 1 hour before being ultrafiltered through an Amicon stirred cell. The retentate was washed with 170 mL of depyrogenated distilled water, before being concentrated to 30 mL and freeze dried.

A reduction in pyrogen of 99% (as measured by LAL) was noted.

EXAMPLE 9

Depyrogenation of Fucoidan Purified from *Undaria pinnatifida* by Contact with High Level Alkali, Followed by Ultrafiltration Fucoidan (2.00 g) was dissolved in 100 mL of 0.5 M NaOH with warming to 40° C. After 10 minutes, the solids were separated by centrifugation and discarded. The supernatant was filtered through a glass fibre filter and a 50 mL aliquot heated to 60° C. for 3 hours. The reaction mixture was then diluted to 100 mL with depyrogenated distilled water and ultrafiltered through an Amicon stirred cell to a concentration of 5 mL. The retentate was then washed with 75 mL of depyrogenated distilled water, concentrated to 5 mL and freeze dried.

A reduction in pyrogen of >99% (as measured by LAL) was noted.

EXAMPLE 10

Depyrogenation of Fucoidan Purified from *Undaria pinnatifida* by Contact with Low Level Peroxide, and High Level Alkali, Followed by Ultrafiltration Fucoidan (2.00 g) was dissolved in 100 mL of 0.5 M NaOH with warming to 40° C. After 10 minutes, the solids were separated by centrifugation and discarded. The supernatant was filtered through a glass fibre filter and a 50 mL aliquot was treated with 1.00 mL of 30% w/w $H_2O_2$ at 60° C. for 3 hours. The reaction mixture was then diluted to 100 mL with depyrogenated distilled water and ultrafiltered through an Amicon stirred cell to a concentration of 5 mL. The retentate was then washed with 75 mL of depyrogenated distilled water, concentrated to 5 mL and freeze dried.

A reduction in pyrogen of >99% (as measured by LAL) was noted.

EXAMPLE 11

Depyrogenation of Fucoidan Purified from *Ecklonia maxima* by Contact with Low Level Peroxide, and High Level Alkali, Followed by Ultrafiltration Fucoidan (8.00 g) was dissolved in 400 mL of 0.5 M NaOH with warming to 45° C. After 10 minutes, the solution was treated with 4.00 mL of 30% w/w $H_2O_2$ at 65° C. for 1 hour. The reaction mixture was then filtered through a glass fibre filter. The pH of the filtrate was adjusted from 13.0 to 10.5 with 50% $H_2SO_4$ and then ultrafiltered through an Amicon stirred cell and concentrated to a volume of 20 mL. The retentate was then washed with 50 mL of depyrogenated distilled water and re-concentrated to 20 mL. The 50 mL wash and reconcentration was repeated a further 2 times. The final concentrated retentate was then freeze dried.

EXAMPLE 12

Depyrogenation of Fucoidan Purified from *Fucus vesiculosus* by Contact with Low Level Peroxide, and High Level Alkali, Followed by Ultrafiltration Fucoidan (6.3 g) was dissolved in 300 mL of 0.5 M NaOH with warming to 45° C. The reaction mixture was heated to 65° C. and treated with 2.00 mL of 30% w/w $H_2O_2$ for 1 hour. The reaction mixture was then filtered through a glass fibre filter. The pH of the filtrate was adjusted from 11.7 to 11.0 with 50% $H_2SO_4$ and then ultrafiltered through an Amicon stirred cell and concentrated to a volume of 20 mL. The retentate was then washed with 50 mL of depyrogenated distilled water and re-concentrated to 20 mL. The 50 mL wash and reconcentration was repeated a further 2 times. The final concentrated retentate was then freeze dried.

A reduction in pyrogen of >99% (as measured by LAL) was noted.

EXAMPLE 13

Depyrogenation of Fucoidan Purified from *Ascophyllum nodosum* by Contact with High Level Peroxide, and High Level Alkali, Followed by Ultrafiltration Fucoidan (15.0 g) was dissolved in 735 mL of 0.5 M NaOH with warming to 40° C. The reaction mixture was centrifuged and the supernatant filtered through Dicalite filter-aid. The filtrate was heated to 60° C. and treated with 30.0 mL of 30% w/w $H_2O_2$ for 1 hour. The reaction mixture at pH 10.0 was then filtered through a glass fibre filter. The filtrate was then ultrafiltered through an Amicon stirred cell and concentrated to a volume of 30 mL. The retentate was then washed with 50 mL of depyrogenated distilled water and re-concentrated to 30 mL. The 50 mL wash and reconcentration was repeated a further 2 times. The final concentrated retentate was then freeze dried.

EXAMPLE 14

Depyrogenation of Fucoidan Purified from *Alaria esculente* by Contact with Low Level Peroxide, and High Level Alkali, Followed by Ultrafiltration Fucoidan (4.0 g) was dissolved in 200 mL of 0.5 M NaOH with warming to 40° C. The reaction mixture was centrifuged and the supernatant filtered through Dicalite filter-aid. The filtrate was heated to 60° C. and treated with 5.0 mL of 30% w/w $H_2O_2$ for 30 minutes. The reaction mixture at pH 10.7 was then filtered through a glass fibre filter. The filtrate was then ultrafiltered through an Amicon stirred cell and concentrated to a volume of 30 mL. The retentate was then washed with 50 mL of depyrogenated distilled water and re-concentrated to 30 mL. The 50 mL wash and reconcentration was repeated a further 2 times. The final concentrated retentate was then freeze dried.

EXAMPLE 15

Depyrogenation of Fucoidan Purified from *Ecklonia radiata* by Contact with Low Level Peroxide, and High Level Alkali, Followed by Ultrafiltration Fucoidan (4.0 g) was dissolved in 200 mL of 0.5 M NaOH with warming to 40° C. The reaction mixture was centrifuged and the supernatant filtered through Dicalite filter-aid. The filtrate was heated to 60° C. and treated with 2.0 mL of 30% w/w $H_2O_2$ for 30 min. The reaction mixture at pH 10.7 was then filtered through a glass fibre filter. The filtrate was then ultrafiltered through an Amicon stirred cell and concentrated to a volume of 30 mL. The retentate was then washed with 50 mL of depyrogenated distilled water and re-concentrated to 30 mL. The 50 mL wash and reconcentration was repeated a further 2 times. The final concentrated retentate was then freeze dried.

EXAMPLE 16

Depyrogenation of Fucoidan Purified from *Sargassum fusiforme* by Contact with Low Level Peroxide, and High Level Alkali, Followed by Ultrafiltration Fucoidan (4.0 g) was dissolved in 200 mL of 0.5 M NaOH with warming to 40° C. The reaction mixture was centrifuged and the supernatant filtered through Dicalite filter-aid. The filtrate was heated to 70° C. and treated with 0.7 mL of 30% w/w $H_2O_2$ for 30 minutes. The reaction mixture was then filtered through a glass fibre filter. The filtrate was then ultrafiltered through an Amicon stirred cell and concentrated to a volume of 30 mL. The retentate was then washed with 50 mL of depyrogenated distilled water and re-concentrated to 30 mL. The 50 mL wash and reconcentration was repeated a further 2 times. The final concentrated retentate was then freeze dried.

EXAMPLE 17

Depyrogenation of Fucoidan Purified from *Macrocystis pyrifera* by Contact with Low Level Peroxide, and High Level Alkali, Followed by Ultrafiltration Fucoidan (2.0 g) was dissolved in 200 mL of 0.5 M NaOH with warming to 40° C. The reaction mixture was then heated to 65° C. and treated with 1.0 mL of 30% w/w $H_2O_2$ for 30 minutes. The reaction mixture was then filtered through a glass fibre filter. The filtrate was then ultrafiltered through an Amicon stirred cell and concentrated to a volume of 30 mL. The retentate was then washed with 50 mL of depyrogenated distilled water and re-concentrated to 30 mL. The 50 mL wash and reconcentration was repeated a further 2 times. The final concentrated retentate was then freeze dried.

EXAMPLE 18

Depyrogenation of Fucoidan Purified from *Cladosiphon okamuranus* by Contact with Low Level Peroxide, and High Level Alkali, Followed by Ultrafiltration Fucoidan (4.0 g) was dissolved in 200 mL of 0.5 M NaOH with warming to 40° C. The reaction mixture was centrifuged and the supernatant filtered through dicalite filter-aid. The filtrate was heated to 65° C. and treated with 2.0 mL of 30% w/w $H_2O_2$ for 30 minutes. The reaction mixture was then filtered through a glass fibre filter. The filtrate was then ultrafiltered through an Amicon stirred cell and concentrated to a volume of 30 mL. The retentate was then washed with 50 mL of depyrogenated distilled water and re-concentrated to 30 mL. The 50 mL wash and reconcentration was repeated a further 2 times. The final concentrated retentate was then freeze dried.

EXAMPLE 19

Depyrogenation of Ulvan Purified from *Ulva* sp. by Contact with Low Level Peroxide, and High Level Alkali, Followed by Ultrafiltration Ulvan (2.0 g) was dissolved in 150 mL of 0.5 M KOH with warming to 55° C. The filtrate was heated to 65° C. and treated with 6.0 mL of 30% w/w H2O2 for 60 minutes. The reaction mixture was then neutralised from pH 12.1 to pH 7.8 with 50% $H_2SO_4$. The filtrate was then ultrafiltered through an Amicon stirred cell and concentrated to a volume of 30 mL. The retentate was then washed with 50 mL of depyrogenated distilled water and re-concentrated to 30 mL. The 50 mL wash and reconcentration was repeated a further 3 times. The final concentrated retentate was then filtered through a 0.2 pm filter and freeze dried.

A reduction in pyrogen of >99% (as measured by LAL) was noted.

EXAMPLE 20

Depyrogenation of Fucoidan Purified from *Fucus vesiculosus*

The starting material was a freeze dried product previously purified for fucoidan, to about 95%, comprising neutral carbohydrates (approximately 60.1%-54.0% fucose, 3.0% galactose), sulfate (27.5%), and counterions (7.5%).

All water used in this method was purified by distillation before use. All equipment was sanitised and rinsed with purified water before use.

1.99 kg of the freeze dried fucoidan product was dissolved in 50-fold (100 L) of 0.04 M KOH.

The dissolution was carried out by firstly placing about 100 L of purified water in a reaction vessel. 4 L of 50% KOH was added to the purified water, and the solution was heated to 60° C. The solid fucoidan (1.99 kg) was then added while mixing. The solution was maintained at 60° C. while mixing until all solids were completely dissolved. The solution had attained a pH of 11.9.

0.5 L of $H_2O_2$ (50%) was added to the filtrate, and the solution held at 65° C. for 1 hour while mixing. The solution was then pH adjusted from 11.9 to 9.5 to 10.0 with $H_2SO_4$ (50% w/w, 3.35 L). A final pH of 9.8 was achieved. The solution was then let cool to 45° C.

The pH adjusted solution was ultrafiltered using three membranes of 78 ft$^2$ each, with nominal cut-off of 5 kDa (Koch, Mass.)

The UF equipment was assembled and sanitized by recirculating 100 L of a solution of 0.05% w/w KOH, followed by 100 L of a solution of 100 ppm NaOCl in at 45 to 50° C., and finally, 100 L of a solution of 0.1% w/w $H_2O_2$, each for 15 minutes. The equipment was then rinsed with at least 200 L of purified water. The fucoidan solution was added to the retentate vessel, and ultrafiltration performed until the retentate was concentrated to about 30% of the original volume. The retentate pressure was maintained at 50 psi through the ultrafiltration step. The permeate flux started at 2.0 L/minute, and was 1.6 L/minute at the conclusion of the ultrafiltration.

The concentrated fucoidan solution (30 L) was then diafiltered using purified water (120 L in 10 L portions). Retentate pressure was maintained at 50 psi. The permeate flux remained at 1.5 L/minute over 7 minutes.

The solution was then concentrated down to a final volume of 22 L.

The concentrate was then freeze dried. A total of 820 g of solid was recovered.

A process yield of 41% was calculated. A reduction in pyrogen of 99% (as measured by LAL) was noted.

EXAMPLE 21

Depyrogenation and Fractionation of Fucoidan Purified from *Fucus vesiculosus* by Contact with Low Level Peroxide, and High Level Alkali, Followed by Two-stage Ultrafiltration Fucoidan (50 g) was dissolved in 2 L of 1% w/w $H_2SO_4$, with warming to 50° C. The reaction mixture was stirred for 1 hour at this temperature. The solution pH was raised from 1.2 to 4.0 by addition of 50% w/w NaOH.

A further 50 g of solid NaOH was added, and the reaction mixture heated to 65° C., over 10 minutes. $H_2O_2$ (26 mL, 30% w/w) was added, and the reaction mixture stirred for a further hour.

The solution pH was lowered from 12.0 to 10.5 by the addition of 50% w/w $H_2SO_4$, allowed to cool overnight, then ultrafiltered using an Advantec AMI UHP stirred cell.

The reaction mixture was first concentrated to 500 mL using a 30 kDa membrane, then the retentate (>30 kDa fraction) washed with 500 mL of distilled water and re-concentrated to 500 mL. The washing/re-concentration was repeated a further three times. The permeate (<30 kDa fraction) underwent the same procedure of concentrating, followed by washing and re-concentrating, four times, this time using a 10 kDa membrane. The final retentates (both 10-30 kDa and >30 kDa fractions) was collected and freeze-dried.

A reduction in pyrogen of 98% (as measured by LAL) was noted for both fractions.

EXAMPLE 22

In situ Isolation, Purification and Depyrogenation of Fucoidan from *Undaria pinnatifida* by Contact with Low Level Peroxide, and High Level Alkali, Followed by Ultrafiltration Seaweed (5.0 g, Undaria pinnatifida) was suspended in 100 g of 0.5% w/w $H_2SO_4$ that had previously been heated to 55° C. The resulting suspension at pH 1.8 was stirred for 4 hours at 50° C. and then filtered through a cellulose filter coated in diatomaceous earth. The pH of the filtrate was then raised to 11.0 with 10% w/w NaOH and the solution heated, with stirring, to 45° C. To this solution, 0.5 mL of 30% w/w $H_2O_2$ was added, and the solution pH maintained above pH 10.9 via addition of 10% w/w NaOH. After 1 hour the solution was removed from heating and the pH reduced to 5.01 with 10% w/w $H_2SO_4$. The cooled solution was then filtered through an Amicon stirred cell and the retentate washed with 50 mL of depyrogenated distilled water three times before being concentrated to 50 mL and freeze dried. An isolated yield of purified white fucoidan of 10.8% was obtained.

It will be appreciated that while the present invention has been described in terms of a number of discrete aspects, with certain embodiments and/or preferred features being disclosed with respect to each aspect, it is contemplated that any of the various embodiments or preferments could be implemented in conjunction with any aspect. Furthermore, the features of any given aspect may be implemented with the features of any other aspect.

While some embodiments described herein include some but not other features included in other embodiments, combinations of features of different embodiments are intended to be within the scope of the invention, and form different embodiments, as would be understood by those in the art.

The invention claimed is:

1. A method of reducing pyrogenicity of a seaweed extract comprising a sulphated polysaccharide molecule having a biological activity and a pyrogenic agent, the method comprising: contacting the seaweed extract with an amount of an oxidant and a base effective to (i) reduce pyrogenicity of the seaweed extract and (ii) maintain at least a proportion of the biological activity of the sulphated polysaccharide molecule.

2. The method of claim 1 comprising contacting the extract with one or more of the following: a surfactant, an activated carbon, a zeolite.

3. The method of claim 2 wherein the oxidant is a peroxide.

4. The method of claim 2 wherein the surfactant is a non-ionic surfactant.

5. The method of claim 2 wherein the base is used in an amount sufficient to result in a pH of greater than about 7.0 and less than about 12.5.

6. The method of claim 1 further comprising contacting the extract with an effective amount of an oxidant, a base and a surfactant.

7. The method of claim 1 further comprising contacting the extract with an effective amount of an activated carbon and a base.

8. The method of claim 1 wherein the extract comprises a plurality of sulphated polysaccharide molecules, and at least about 30% of the plurality of sulphated polysaccharide molecules is recovered from the treated extract.

9. The method of claim 1 wherein at least about 50% of the pyrogenic agent is removed and/or inactivated.

10. The method of claim 1 wherein the sulphated polysaccharide molecule is, a fucoidan or an ulvan.

\* \* \* \* \*